(12) United States Patent
Kong

(10) Patent No.: US 8,633,018 B2
(45) Date of Patent: Jan. 21, 2014

(54) FUSION PROTEIN CONTAINING A SINGLE-STRANDED DNA BINDING PROTEIN AND METHODS FOR EXPRESSION AND PURIFICATION OF THE SAME

(76) Inventor: Daochun Kong, Rockville, MD (US)

( * ) Notice: Subject to any disclaimer, the term of this patent is extended or adjusted under 35 U.S.C. 154(b) by 0 days.

(21) Appl. No.: 12/605,389

(22) Filed: Oct. 26, 2009

(65) Prior Publication Data

US 2011/0237777 A1  Sep. 29, 2011

(51) Int. Cl.
  *C12N 15/00* (2006.01)
  *C07H 21/02* (2006.01)
  *C07K 14/00* (2006.01)

(52) U.S. Cl.
  USPC .................. 435/320.1; 536/23.1; 530/350

(58) Field of Classification Search
  USPC .................. 435/320.1; 536/23.1; 530/350
  See application file for complete search history.

(56) References Cited

U.S. PATENT DOCUMENTS 5,543,264 A * 8/1996 Anderson et al. ............. 435/219
2009/0176205 A1 * 7/2009 Nishimura et al. ............... 435/6

OTHER PUBLICATIONS

Wang et al. 2007; Calling cards for DNA binding proteins. Genome Research. 17:1202-1209.*
Novy et al. 2007 at www.ccbi.cam.ac.uk/iGEM2007/images/8/89/NovagenCBDVectors.pdf.*
GE Healthcare 2011 at www.gelifesciences.com/aptrix/upp01077.nsf/content/Products?OpenDocument&parentid=976038&moduleid=38859&zone=Proteomics.*
Novagen, 2012 at www.emdchemicals.com/life-science-research/pet-gst-fusion-system-41/EMD_BIO-70559/p_.Fub.s1Op64AAAEj6xt9.zLX.*
Wang et al. 2007; Calling cards for DNA binding proteins. Genome Research 17: 1202-1209.*

* cited by examiner

*Primary Examiner* — Karen Cochrane Carlson

(57) ABSTRACT

The present invention provides an expression vector comprising a promoter and a polynucleotide sequence encoding a fusion protein. The present invention further provides a method for purification of an interest protein. The present invention also provides a fusion protein comprising a single-stranded DNA binding protein and an interest protein or polypeptide fused directly or indirectly with the COOH-terminus or NH$_2$-terminus of the single-stranded DNA binding protein, wherein said fusion protein is capable of binding to single-stranded DNA.

9 Claims, 13 Drawing Sheets

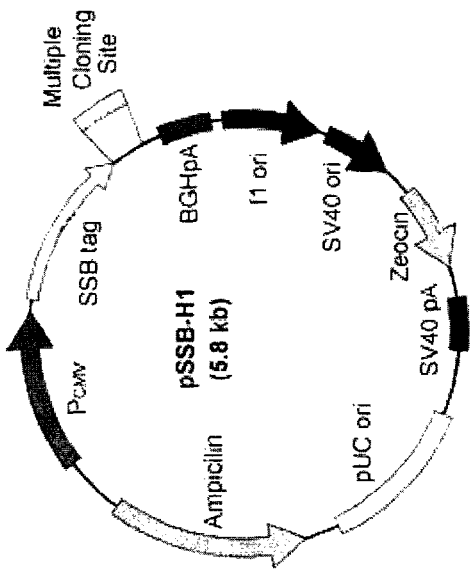

| | | | | | |
|---|---|---|---|---|---|
| pSSB-H1 | CTC GAG<br>XhoI | GCT......TTC<br>SSB tag | GAC GAC GAC AAG<br>enterokinase | GGA TCC<br>BamHI | AGT GAA TTC CTG CAG<br>EcoRI  KpnI |
| pSSB-H2 | CTC GAG<br>XhoI | GCT......TTC<br>SSB tag | CTG GTG CCG CGC GGC AGC<br>thrombin | GGA TCC<br>BamHI | AGT GAA TTC CTG CAG<br>EcoRI  KpnI |
| pSSB-H3 | CTC GAG<br>XhoI | CAT CAC CAC CAT CAC CAT<br>6 His tag | GCT......TTC<br>SSB tag | GAC GAC GAC AAG<br>enterokinase | GGA TCC AGT GAA TTC CTG CAG<br>BamHI  EcoRI  KpnI |
| pSSB-H4 | CTC GAG<br>XhoI | CAT CAC CAC CAT CAC CAT<br>6 His tag | GCT......TTC<br>SSB tag | CTG GTG CCG CGC GGC AGC<br>thrombin | GGA TCC AGT GAA TTC CTG CAG<br>BamHI  EcoRI  KpnI |

FUSION PROTEIN CONTAINING A
SINGLE-STRANDED DNA BINDING
PROTEIN AND METHODS FOR EXPRESSION
AND PURIFICATION OF THE SAME

FIELD OF THE INVENTION

The present invention generally relates to the technologies of protein expression and purification, and more particularly to a fusion protein containing a single-stranded DNA binding protein and methods for expression and purification of the fusion proteins containing a single-stranded DNA binding protein.

BACKGROUND OF THE INVENTION

Due to the availability of entire genomic DNA sequences in numerous organisms and the advance of recombinant DNA technology, it has become simple to clone any genes and subsequently overexpress them in prokaryotic or eukaryotic cells. The biochemical elucidation of protein functions requires obtaining proteins with high purity.

A number of approaches have been developed for the isolation and purification of proteins, particularly recombinant proteins, from other components of a biological sample. The approaches include ion exchange chromatography based on molecular charges, gel filtration based on molecular size, and affinity chromatography. The affinity chromatography is more specific and much more efficient than the other purification approaches because it makes use of the specific affinity of a protein for a purifying reagent such as an antibody or ligand to which it specifically binds. One member of a binding pair may be used to "tag" a protein of interest, with the other member used as an affinity ligand. Such a protein "tag" may be "fused" recombinantly and expressed to produce a fusion protein with the tag attached. The "tagged" fusion protein is then affinity purified by interaction with the binding partner of the tag and the tag is then optionally cleaved to release pure protein. However, the known affinity chromatography suffers from the drawbacks such as unsatisfactory purity, time-consuming, high cost and/or unusual elution conditions.

SUMMARY OF THE INVENTION

Therefore, there is a need to provide a method and system for simply, efficiently and economically expressing and purifying recombinant proteins.

One aspect of the present invention provides an expression vector comprising a promoter and a polynucleotide sequence encoding a fusion protein; wherein the fusion protein-encoding polynucleotide sequence is so operably linked to the promoter that the transcription of the fusion protein-encoding polynucleotide sequence is controlled by the promoter; wherein the fusion protein comprises a single-stranded DNA-binding protein and an interest protein or polypeptide fused directly or indirectly with the COOH-terminus or NH$_2$-terminus of the single-stranded DNA-binding protein; and wherein the fusion protein is capable of binding to single-stranded DNA.

Another aspect of the present invention provides a method for purification of an interest protein. In one embodiment, the method comprises contacting a host cell with an expression vector, wherein the expression vector comprises a promoter and a polynucleotide sequence operably linked to the promoter, wherein the polynucleotide sequence encodes a fusion protein comprising a single-stranded DNA binding protein and the interest protein fused directly or indirectly with the COOH-terminus or NH$_2$-terminus of the single-stranded DNA binding protein, and wherein the fusion protein is capable of binding to single-stranded DNA; culturing the host cell under such conditions that the fusion protein is expressed; lysing the host cell to obtain a cell lysate; contacting the cell lysate with a substrate immobilized with single-stranded DNA to allow the fusion protein to bind to the single-stranded DNA of the substrate; washing the substrate to remove impurities; and eluting the bound fusion protein from the substrate; thereby the interest protein is expressed and purified in the form of the fusion protein.

Another aspect of the present invention provides a fusion protein comprising a single-stranded DNA binding protein and an interest protein or polypeptide fused directly or indirectly with the COOH-terminus or NH$_2$-terminus of the single-stranded DNA binding protein, wherein said fusion protein is capable of binding to single-stranded DNA; thereby the fusion protein can be purified by a substrate immobilized with single-stranded DNA.

The present invention has apparent advantages. First, the fusion protein is soluble and can be purified from cell lysates under physiological condition by affinity chromatography on a column of single-stranded DNA (ssDNA) cellulose. Second, the separation of the said fusion protein from other proteins and impurities existed in cell lysates through one step of ssDNA-cellulose chromatography is highly efficient, apparently more efficient than the other affinity chromatography such as $Ni^{2+}$-agarose column. Third, the fusion protein can be eluted from ssDNA-cellulose by just raising salt (NaCl or KCl) concentration. The recovery of the said fusion proteins from ssDNA-cellulose is very efficient and simple.

The objectives and advantages of the invention will become apparent from the following detailed description of preferred embodiments thereof in connection with the accompanying drawings.

BRIEF DESCRIPTION OF THE DRAWINGS

Preferred embodiments according to the present invention will now be described with reference to the Figures, in which like reference numerals denote like elements.

FIG. 1D shows the structure of the series of expression vectors of pSSB-H, including the schematic representation of pSSB-H1. This series of plasmids are applicable in human cells. Also shown are the specific protease cleavage sites among the vectors of pSSB-H1, pSSB-H2, pSSB-H3, and pSSB-H4. An additional 6His-tag is located at the N-terminus of the SSB in pSSB-H3 and pSSB-H4 vectors. The multiple enzymatic linkers in pSSB-H1, pSSB-H2, pSSB-H3 and pSSB-H4 are listed as SEQ ID NOs 13, 14, 15 or 16 respectively.

DETAILED DESCRIPTION OF THE INVENTION

Figure 1A:
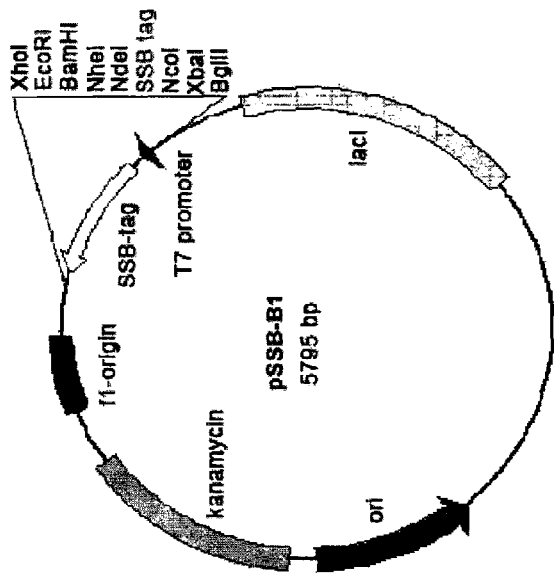
FIG. 1A shows the structure of the series of expression plasmid vectors of pSSB-B, including the schematic representation of pSSB-B1. This series of plasmids are applicable in bacteria. Also shown are the specific protease cleavage sites among the vectors of pSSB-B1, pSSB-B2, pSSB-B3, pSSB-B4. An additional 6His-tag is located at the N-terminus of the SSB in pSSB-B3 and pSSB-B4 vectors. The multiple enzymatic linkers in pSSB-B1, pSSB-B2, pSSB-B3 and pSSB-B4 are listed as SEQ ID NOs 3, 4, 5, or 6 respectively.

The present invention may be understood more readily by reference to the following detailed description of certain embodiments of the invention.

Throughout this application, where publications are referenced, the disclosures of these publications are hereby incorporated by reference, in their entireties, into this application in order to more fully describe the state of art to which this invention pertains.

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, for example, *Molecular Cloning: A Laboratory Manual*, second edition (Sambrook et al., 1989); *Current Protocols in Molecular Biology* (F. M. Ausubel et al., eds., 1987).

One aspect of the present invention provides expression vectors for expression of fusion proteins in host cells such as prokaryotic organisms (e.g., E. coli), and eukaryotic cells (e.g., yeast, insect, and mammalian cells). A "fusion protein" is a chimeric molecule in which the constituent molecules are all polypeptides and are attached (fused) to each other such that the chimeric molecule forms a continuous single chain. The various constituents can be directly attached to each other or can be coupled through one or more peptide linkers. A "linker" as used in reference to a chimeric molecule refers to any molecule that links or joins the constituent molecules of the chimeric molecule. Where the chimeric molecule is a fusion protein, the linker may be a peptide that joins the proteins comprising a fusion protein.

The fusion proteins comprise a single-stranded DNA binding protein (SSB). The SSB used herein refers to any protein or polypeptide that is capable of binding to single-stranded DNA; thus when an interest protein or polypeptide is fused to the C-terminal or N-terminal of the SSB, it can be purified by the binding of SSB to the single-stranded DNA. When the single-stranded DNA is immobilized onto a substrate, an effective affinity chromatography system for purification of SSB-containing fusion proteins can be established; thereby the interest proteins can be easily expressed and purified.

The SSB suitable for the present invention may be derived from natural SSBs that exist almost in all organisms and are normally expressed as part of the genomic functions. For example, bacteriophage T7 expresses a single-stranded DNA binding protein (SEQ ID NOs 1 and 2) with a molecular weight of 25.6 kDa (Dunn J J, Studier F W (1983) Complete nucleotide sequence of bacteriophage T7 DNA and the location of T7 genetic elements. *J Mol Biol.* 166(4):477-535). In a physiological condition, it exists as a homo-dimer and is a very soluble protein. It specifically binds to ssDNA with high affinity and without sequence preference. At 1.0 M of salt concentration, T7 SSB dissociates from ssDNA. The SSBs used in the fusion proteins may be a fragment, mutated form, or a variant of the natural ones. The suitable SSBs may be selected from artificial sequence libraries such as phage display by assaying their capabilities of binding to single-stranded DNAs. The selected sequences may be advantageous over the natural ones when the selected sequences are smaller so that there is no need to remove the SSB from the fusion protein. In many cases, there may be no need to remove the SSB if the SSB-tagged fusion protein has normal biological activities and functions.

In certain embodiments, the fusion protein comprises a cleavable linker that is disposed between the SSB and interest protein, affording the removal of the SSB from the fusion protein by chemical or enzymatic treatment of the fusion protein. It is apparent that the cleavable linker can be disposed at any site of the fusion protein according to a user's desire. In the expression vectors, the cleavable linker comprises a DNA sequence which codes for an amino acid or a sequence of amino acids which can be cleaved chemically or enzymatically at its C-terminal.

Examples of chemical agents useful for cleaving proteins are cyanogen bromide, 2-(2-nitrophenylsulfenyl)-3-bromo-3'-methylindolinium (BNPS-skatole), hydroxylamine, and the like. Cyanogen bromide cleaves proteins at the C-terminal of a methionine residue. BNPS-skatole cleaves at the C-terminal of a tryptophan residue. Hydroxylamine cleaves at the C-terminal of the moiety -Asn-Z- in which Z is Gly, Leu, or Ala.

Examples of enzymatic agents useful for cleavage are trypsin, papain, pepsin, plasmin, thrombin, enterokinase, and the like. Each effects cleavage at a particular amino acid sequence which it recognizes. Enterokinase, for example, recognizes the amino acid sequence -(Asp)$_n$-Lys- in which n is an integer from 2 to 4.

In certain embodiments, the fusion protein comprises one or more other purification tags. For example, six histidine residues are fused to the SSB at its N- or C-terminals, allowing purification of the SSB-containing fusion protein by a combination of Ni$^{2+}$ column and single-stranded DNA-immobilized substrate. After the purification, the portion of SSB and six histidine residues can be removed by chemical or enzymatic cleavage. In fact, any known purification tag is suitable here including myc tag, HA tag, Flag-peptide, KT3 epitope, alpha-tubulin epitope, T7 gene 10 protein peptide tag, glutathione-5-transferase (GST), strep-tag, bovine pancreatic trypsin inhibitor (BPTI), and maltose binding protein (MBP).

The expression vectors are nucleic acid constructs, generated recombinantly or synthetically, with nucleic acid elements that are capable of effecting expression of a gene or cDNA in hosts compatible with such sequences. The recombinant expression vector includes one or more regulatory sequences operably linked to the nucleic acid encoding the enzyme(s) in a manner that allows for transcription of the nucleic acid into mRNA and translation of the mRNA into the subject proteins. The term "regulatory sequences" is art-recognized and intended to include promoters, and/or enhancers and/or other expression control elements (e.g., polyadenylation signals). Such regulatory sequences are known to those skilled in the art (see, e.g., Goeddel (1990) Gene Expression Technology: Meth. Enzymol. 185, Academic Press, San Diego, Calif.).

Figure 1B:
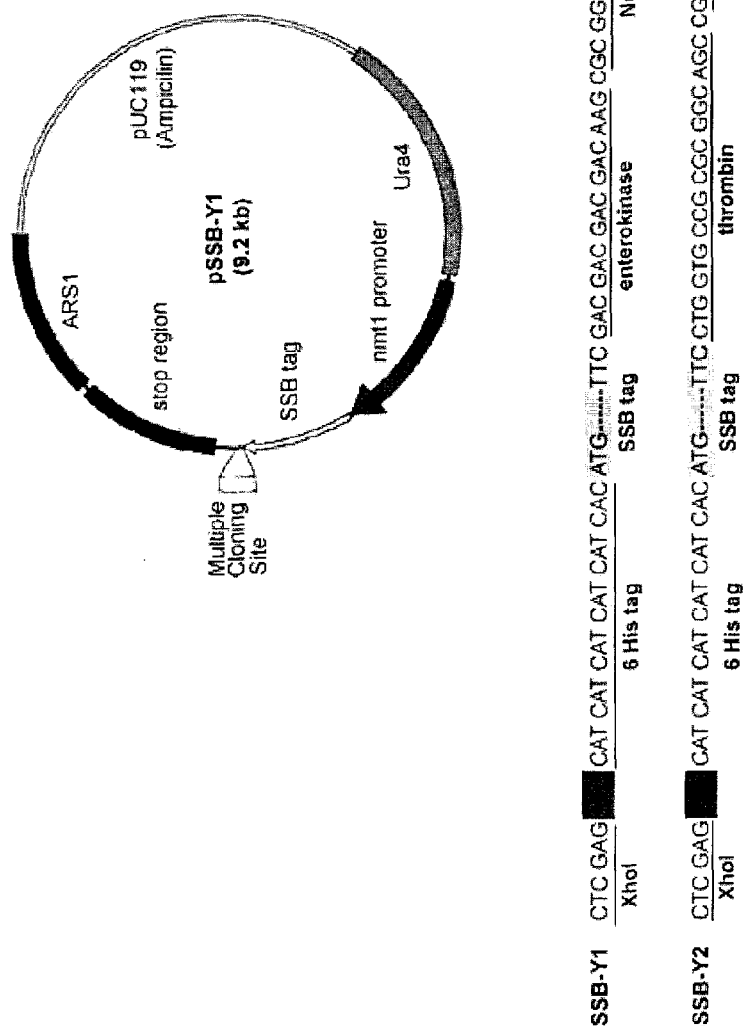
FIG. 1B shows the structure of the series of expression vectors of pSSB-Y, including the schematic representation of pSSB-Y1. This series of plasmids are applicable in the fission yeast S. pombe. The positions of 6 His tag, SSB, enterokinase or thrombin cleavage site, and multiple cloning sites are also indicated in a portion of pSSB-Y1 or pSSB-Y2 expression vector. The multiple enzymatic linkers in pSSB-Y1 and pSSB-Y2 are listed as SEQ ID NOs 7 or 8 respectively.
Figure 1C:
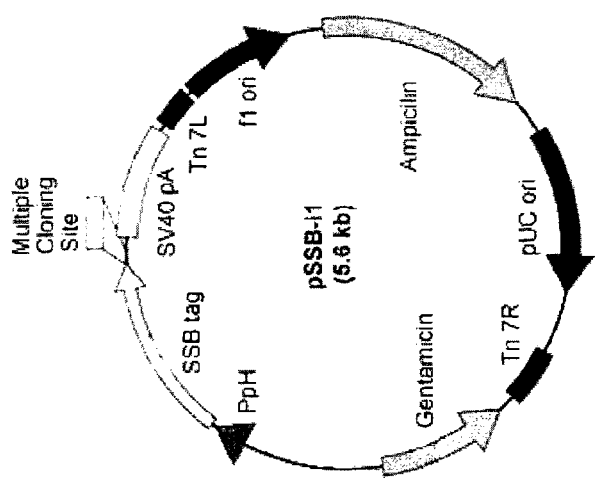
FIG. 1C shows the structure of the series of expression vectors of pSSB-I, including the schematic representation of pSSB-I1. This series of plasmids are applicable in insect cells. Also shown are the specific protease cleavage sites among the vectors of pSSB-I1, pSSB-I2, pSSB-I3, pSSB-I4. An additional 6His-tag is located at the N-terminus of the SSB in pSSB-I3 and pSSB-I4 vectors. The multiple enzymatic linkers in pSSB-I1, pSSB-I2, pSSB-I3 and pSSB-I4 are listed as SEQ ID NOs 9, 10, 11 or 12 respectively.

In certain embodiments, the expression vectors are a series of plasmid expression vectors (pSSB) that have been constructed to guarantee SSB-tagged fusion proteins to be expressed in a wide range of host cells: pSSB-B1-B4 for bacteria, pSSB-Y1-Y2 for yeast, pSSB-I1-I4 for insect cells, and pSSB-H1-H4 for mammalian cells (FIG. 1). A typical expression vector before incorporating a DNA sequence encoding for an interest protein contains: 1) a promoter region, 2) a 5' untranslated region, 3) a protein-coding region, 4) a 3' untranslated region, and 5) a transcription termination site. The "protein-coding region" is so constructed that interest protein sequence can be easily inserted to form a fusion protein. For example, the "protein-coding region" includes a 696 bp DNA fragment of Bacteriophage T7 gp2.5 gene encoding for SSB (SEQ ID NO 1). In certain embodiments, a specific protease (thrombin or enterokinse) recognition linker is inserted near the C-terminal of SSB. Multiple cloning sites are also designed downstream the protease cleavage linker, wherein DNA sequences coding for the desired proteins or polypeptides can be inserted. In addition, other purification tags can also be included in the "protein-coding region". It will be appreciated that desired polypeptides can be operably linked to constitutive promoters or inducible and/or tissue-specific promoters.

In certain embodiments, the expression vectors can be derived from cosmids or viruses. For example, replication defective retroviruses, adenoviruses and adeno-associated viruses can be used Another example of an expression vector is a yeast artificial chromosome (YAC), which contains both a centromere and two telomeres, allowing YACs to replicate as small linear chromosomes. A number of suitable expression systems are commercially available and can be modified to produce the vectors of the present invention. Illustrative expression systems include, but are not limited to, baculovirus expression vectors.

As discussed above, the techniques for expression vector cloning, construction and amplification are well known to those skilled in the art. Therefore, the expression vectors for SSB-tagged fusion proteins can be constructed by routine procedures; no further details are provided herein in order not to obscure the present invention.

Another aspect of the present invention provides a method for purification of an interest protein in the form of a SSB-tagged fusion protein. Due to the nature that DNA exists at a double-stranded state inside cells, there are a lot of proteins able to bind to dsDNA with various degree of affinity while few proteins have the characteristic to bind to ssDNA. SSB is evolutionally selected and designed to bind to and protect ssDNA region at DNA replication forks during DNA replication. Briefly, the expression vectors for the SSB-tagged fusion proteins as described above are introduced into compatible host cells; culture the host cells in appropriate conditions to effect the expression of the SSB-tagged fusion proteins within the host cells; lyse the cells to obtain cell lysates; contact the cell lysates with an affinity substrate immobilized with single stranded DNAs; wash off impurities; and elute the fusion proteins.

As used herein, the term "host cell" is intended to include any cell or cell line into which a recombinant expression vector for production of a SSB-tagged fusion protein may be transfected for expression of a SSB-tagged fusion protein. Suitable host cells include, but are not limited to, algal cells, bacterial cells (e.g., E. coli), yeast cells (e.g., S. cerevisiae, S. pombe), fungal cells, plant cells, invertebrate cells (e.g., insect cells such as SF9 cells, and the like), and vertebrate cells including mammalian cells. In one embodiment, the expression system includes a baculovirus vector expressed in an insect host cell. An in vitro transcription and translation system with cell extracts can also be used to produce the SSB-tagged fusion proteins.

An expression vector encoding a SSB-tagged fusion protein can be introduced into a host cell by standard techniques such as transfection and transformation. All conventional techniques for introducing nucleic acid into host cells are included for the present invention.

The affinity substrate of the present invention comprises immobilized single strand DNAs that serve as the capture ligand for the SSBs in the SSB-tagged fusion proteins. The capture ligand is covalently attached to or associated with a matrix material. Non-limiting examples of matrix materials include solids, gels, pastes, membranes, or slurries. Suitable matrix materials include, but are not limited to, glass, beads, controlled pore glass, magnetic beads, various membranes or rigid various polymeric resins such as polystyrene, polystyrene/latex, and other organic and inorganic polymers, both natural and synthetic. Illustrative polymers include polyethylene, polypropylene, poly(4-methylbutene), polystyrene, polymethacrylate, poly(ethylene terephthalate), rayon, nylon, poly(vinyl butyrate), polyvinylidene difluoride (PVDF), silicones, polyformaldehyde, cellulose, cellulose acetate, and nitrocellulose. Other materials that can be employed, include paper, glass, minerals, ceramics, metals, metalloids, plastics, semiconductive materials, or cements. In addition, substances that form gels, such as proteins (e.g., gelatins), lipopolysaccharides, silicates, agarose, and polyacrylamides can be used Polymers that form several aqueous phases, including, but not limited to, dextrans, polyalkylene glycols or surfactants, such as phospholipids, or long chain alkyl ammonium salts are also suitable.

Preferred matrix materials include resins, such as for example synthetic resins (e.g., cross-linked polystyrene, divinyl benzene, etc.), and cross-linked polysaccharides (e.g., cellulose, dextran (sephadex), agarose, sepharose), and the like. In some embodiments, the matrix material includes reactive groups capable of forming a covalent link with a SSB. In one embodiment, the matrix material includes a glyoxal activated agarose. In another embodiment, the matrix material includes a sulfhydryl reactive group. In another embodiment, the matrix material is activated with cyanogen bromide. In other embodiments, the SSBs are attached to an agarose resin by the use of a cross-linking reagent. Such reagents are well known to those skilled in the art and include carbodiimides, maleimides, succinimides, and reactive disulfides.

An affinity matrix of the present invention can take any convenient form. In certain embodiments, the affinity matrix is packed into a column, a mini-column, or a capillary or microcapillary, or a capillary electrophoresis tube. In some embodiments, the affinity matrix is suspended in one phase of a multiphase solution. In such embodiments, the affinity matrix thus acts to partition the tagged molecule into that particular phase of the multiphase system. Such multi-phase purification systems are well suited to large volume/high throughput applications.

In certain embodiments, the affinity matrix is cellulose. Single-stranded DNA (ssDNA) is immobilized onto the cellulose either covalently or non-covalently. When the ssDNA is bound to the cellulose covalently, the leak or release of the bound ssDNA is minimized. The ssDNA is not necessarily sequence specific. When double-strand DNA (dsDNA) (e.g., salmon sperm DNAs) is used, it is denatured first to obtain ssDNA and then immobilized onto the cellulose to produce ssDNA-cellulose affinity matrix.

In certain embodiments, the whole cell lysate containing the SSB-fusion proteins is applied to ssDNA-cellulose column. The SSB-fusion proteins bind to immobilized ssDNA through SSB while other proteins and impurities go through the column. The bound SSB-fusion protein can be simply eluted by raising salt (KCl or NaCl) concentration. The process of the present invention is naturally efficient to separate interest proteins or polypeptides in the form of SSB-fusion proteins from impurities in cell lysate.

In certain embodiments, ssDNA-cellulose affinity matrix has a capacity of at least 12 mg fusion protein/ml swollen cellulose. The yield of SSB-fusion protein overexpressed in E. coli is between 3 and 30 mg per liter of culture, which varies with different interest protein. ssDNA-cellulose affinity matrix can be used several times for preparation of the same fusion protein or else recycled by washing with 1.5M NaCl. In addition, ssDNA cellulose affinity matrix is in dry state and therefore can be kept in an indefinite time without apparent loss in both binding capacity and the efficiency of separating the SSB-fusion proteins from impurities.

Another aspect of the present invention provides a SSB-fusion protein comprising a SSB and an interest protein fused with the SSB either directly or indirectly. The SSB-fusion protein may further comprise one or more other affinity purification tags and/or a linker for removal of the SSB partner and other affinity purification tags. The SSB-fusion protein may be expressed using the expression vectors and purified using the ssDNA-immobilized affinity matrix or in combination with other affinity matrix such as nickel columns as described above.

The fusion proteins of the present invention may be directly used in subsequent biochemical reactions since the interest proteins or polypeptides retain their antigenicity and functional activity if the SSB portion of fusion proteins does not interfere with a specific biochemical reaction. Alternatively, the fusion protein may be cleaved to remove the SSB portion and provide just the interest proteins or polypeptides. If the production of such interest proteins or polypeptides is desired, a cleavable linker is provided in the fusion protein between the SSB and the interest proteins or polypeptides.

The following examples are provided for the sole purpose of illustrating the principles or implementation of the present invention; they are by no means intended to limit or narrow the scope of the present invention.

Example 1

Construction of Expression Plasmid Vectors pSSB-B1, B2, B3 and B4

The DNA fragment encoding for the single-stranded DNA binding protein (SSB) of bacteriophage T7 (SEQ ID NO 1) was amplified from T7 genomic DNA by polymerase chain reaction (PCR) with two designed primers and inserted into the expression plasmid vector pET28a at Nco1 and BamH1 sites to create the expression vector pSSB-B1. In pSSB-B1 vector, a cleavable linker (SEQ ID NO 3) recognized by the protease enterokinase was placed between the SSB and BamH1 site. With similar method, the expression plasmid vectors of pSSB-B2, B3 and B4 (SEQ ID NOs 4-6) were constructed. In all these four vectors, SSB and a cleavable linker for enterokinase or thrombin were placed between the NcoI and BamHI sites in pET28a vector. In addition, a tag of six histidine residues was placed right at the N-terminus of SSB in the vectors of pSSB-B3 and pSSB-B4. The physical maps and the multiple cloning sites are shown in FIG. 1A. This series of plasmid vectors were used to express the SSB- or 6His-SSB-tagged fusion proteins in E. coli.

Example 2

Construction of Expression Plasmid Vectors pSSB-Y1 and Y2

The DNA fragment encoding for the single-stranded DNA binding protein (SSB) of bacteriophage T7 (SEQ ID NO 1)

was amplified from T7 genomic DNA by polymerase chain reaction (PCR) with designed primers and inserted into the fission yeast expression vector pSLF1072 at the XhoI and NotI sites to create the expression vectors pSSB-Y1 and Y2 (SEQ ID NOs 7 and 8). In pSSB-Y1, a cleavable linker for enterokinase was placed between SSB tag and NotI site; whereas in pSSB-Y2, a cleavable linker for thrombin was placed between SSB tag and NotI site. In addition, a tag of six histidine residues was placed right at the N-terminus of SSB in the vectors of pSSB-Y1 and pSSB-Y2. The physical maps and the sequences of multiple cloning site are shown in FIG. 1B. This series of plasmid vectors were used to express the 6His-SSB-tagged fusion proteins in yeast.

Example 3

Overexpression of Fusion Proteins 6His-SSB-Sap1 and SSB-Fen1 in *E. coli* and Purification of the Fusion Proteins with ssDNA-Cellulose Chromatography Sap 1 (SEQ ID NO 17) is an essential protein relating to DNA replication initiation process, abundant in *Schizosaccharomyces pombe*, and has a molecular weight of 30 kDa. The DNA fragment of the sap1 gene was amplified from the fission yeast genomic DNA by PCR reaction and inserted into pSSB-B4 vector at BamHI and HindIII sites. The recombinant plasmid encoding for the fusion protein 6His-SSB-Sap1 was transformed into *E. coli* BL21(DE3)pLys cells to obtain individual colonies. A single colony was introduced into a 50 ml of liquid LB medium containing 20 μg/ml of Kanamycin and incubated for overnight. The overnight culture was inoculated into fresh medium at the dilution of 1:50 to 1:100 and incubated at 37° C. to $OD_{590}$=~0.3. Then, IPTG was added to 0.1 mM and the culture was incubated for additional 3.5 hrs. The cells were then recovered by centrifugation, resuspended in the buffer A (50 mM Tris-HCl, pH 7.4, 5 mM Magnesium Acetate, 5 mM DTT, 1 mM EDTA, 1 mM EGTA, 0.04% NP-40, 10% glycerol) containing 0.4M KCl, broken by sonication, and spun at 37,000 g for 30 min. The whole cell extract and subsequent pellet and supernatant of the cell lysate were examined by SDS-PAGE electrophoresis. The result shown in FIG. 2 indicated that 1) the amount of 6His-SSB-Sap1 fusion protein in total cellular proteins reached to ~25%; 2) the fusion protein 6His-SSB-Sap1 was very soluble and thus its majority was in the supernatant portion after centrifugation. Since Sap1 is a DNA binding protein, the buffer A containing 0.4 M KCl was used to separate Sap1 from chromatin DNA.

Figure 3:
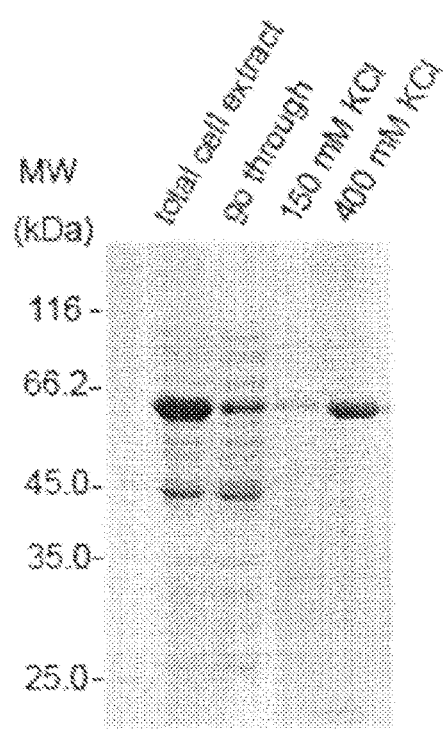
FIG. 3A shows the purification of the fusion protein 6His-SSB-Sap1 through ssDNA-cellulose column. The total cell extracts were applied to the ssDNA-cellulose column. The unbound proteins and other impurities went through the column. The bound 6His-SSB-Sap1 was eluted from ssDNA-cellulose at ~0.4 M KCl.
FIG. 3B shows that 6His-SSB-Sap1 that was already purified by ssDNA-cellulose chromatography bound to $Ni^{2+}$-agarose well and was eluted at 250 mM imidazole. This result indicates that 6His-SSB-Sap1 can be further purified with $Ni^{2+}$-agarose column if it is needed.
Figure 3:
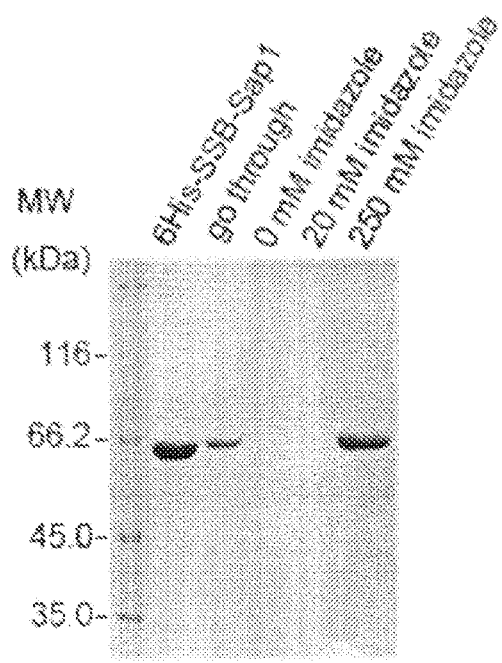

The supernatant portion containing 6His-SSB-Sap1 was adjusted to salt concentration of 0.2 M with buffer A and then applied to ssDNA-cellulose column. The column was washed with buffer A containing 0.2M KCl to remove unbound proteins and other impurities. Then, the bound fusion protein 6His-SSB-Sap1 was eluted at ~0.4 M KCl. As shown in FIG. 3A, after one step of ssDNA-cellulose chromatography the purity of 6His-SSB-Sap1 reached to ~96% as measured by densitometry.

Figure 6:
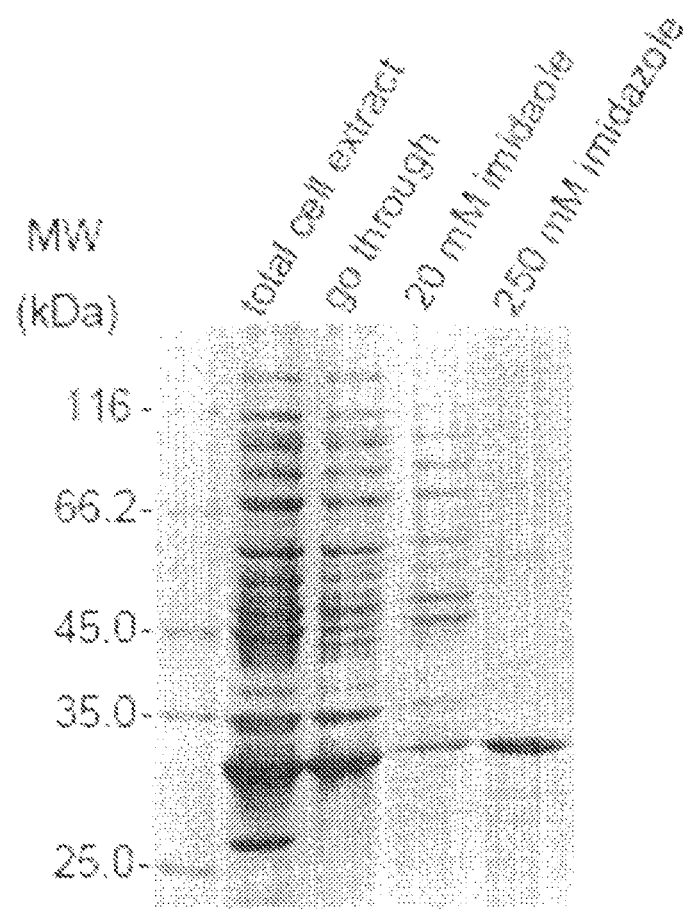
FIG. 6 shows the purification of 6His-Sap1 from cell lysate through $Ni^{2+}$-NTA agarose column. 6His-Sap1 was overexpressed in E. coli cells. The cell extract containing 6His-Sap1 was applied to $Ni^{2+}$-NTA agarose column and the column was washed with several column volumes of buffer containing 20 mM imidazole to remove unbound proteins and other impurities. The bound 6His-Sap1 was eluted at 250 mM imidazole.

To test whether the fusion protein 6His-SSB-Sap1 could bind to $Ni^{2+}$-NTA agarose column through the six histidine residues placed at the N-terminus of the fusion protein, 6His-SSB-Sap1 purified by ssDNA-cellulose affinity chromatography was applied to $Ni^{2+}$-NTA agarose column. As indicated in FIG. 3B, 6His-SSB-Sap1 bound to $Ni^{2+}$ column well and was eluted at 250 mM imidazole. This indicates that 6His-SSB-tagged fusion proteins may be purified with two chromatographic columns of different characteristics. One is ssDNA-cellulose column and the other is $Ni^{2+}$-NTA agarose column. By the combination of ssDNA-cellulose and $Ni^{2+}$-agarose chromatographic columns, 6His-SSB-tagged fusion proteins that are expressed even at low level can be generally purified to high homogeneity for subsequent biochemical characterization.

Figure 4:
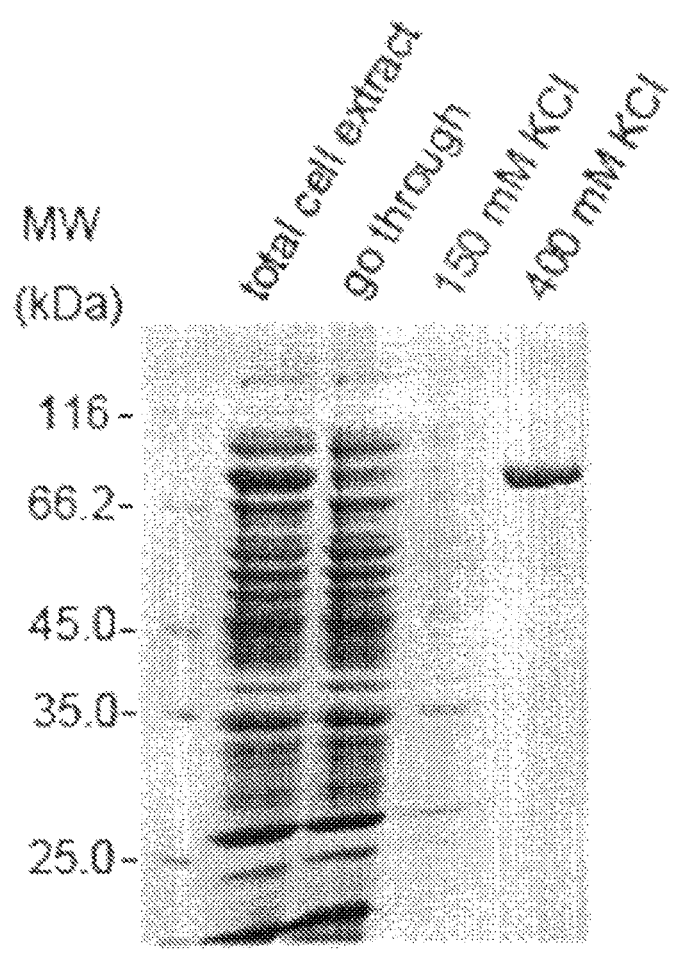
FIG. 4 shows the purification of the fusion protein SSB-Fen1 that was in cell lysate through ssDNA-cellulose chromatography. The Fen1 is human flap endonuclease 1. The fusion protein SSB-Fen1 was overexpressed in E. coli cells. The cell extract containing the SSB-Fen1 was applied to ssDNA-cellulose column. The bound SSB-Fen1 was eluted at ~0.4 M KCl.

With similar procedures, Fen1 gene (SEQ ID NO 18) was inserted into pSSB-B1 vector at SacI and HindIII sites. The fusion protein SSB-Fen1 was overexpressed in *E. coli* BL21 (DE3)pLys cells. Like the fusion protein 6His-SSB-Sap1, SSB-Fen1 was soluble in buffer A containing 0.1 M KCl. As shown in FIG. 4, SSB-Fen1 bound to ssDNA-cellulose well and was eluted at ~0.4 M KCl. Again, with one step of ssDNA-cellulose chromatography the purity of SSB-Fen1 reached to ~96% as measured by densitometry.

Figure 2:
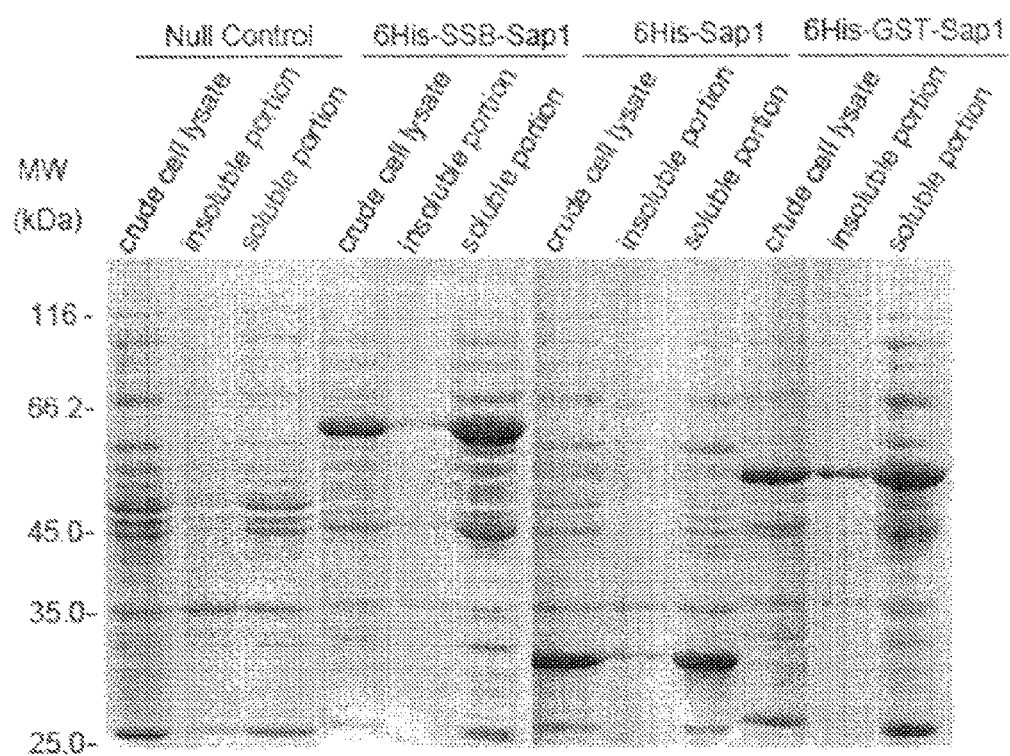
FIG. 2 shows the expression level of the fusion protein 6His-SSB-Sap1, 6His-Sap1 and 6His-GST-Sap1 that were overexpressed in E. coli BL21(DE3)pLys cells. All these three fusion proteins were soluble in cell lysate as indicated in the lanes of soluble portion. A null control without the expression of the fusion proteins is also shown. The MW in all figures is an abbreviation of molecular weight. The kDa is an abbreviation of kilo-Dalton.
Figure 5:
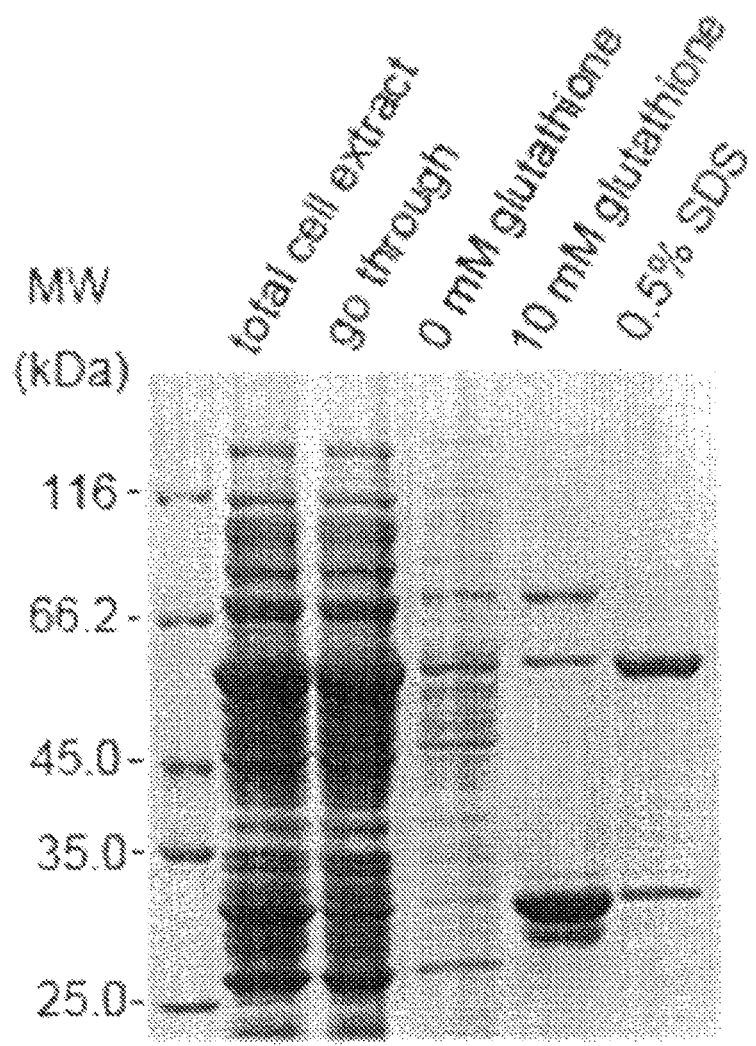
FIG. 5 shows the purification of 6His-GST-Sap1 from cell lysate through glutathione-sepharose 4B. The fusion protein 6His-GST-Sap1 was overexpressed in E. coli cells. The cell extract containing the 6His-GST-Sap1 was applied to Glutathione Sepharose 4B column. After the column was thoroughly washed with a buffer without glutathione, the bound 6His-GST-Sap1 was first eluted with 10 mM glutathione. The 6His-GST-Sap1 that remained binding to the column of Glutathione Sepharose 4B was further eluted by 0.5% SDS.

To compare the efficiency to purify SSB-, GST-, and 6His-tagged fusion proteins with ssDNA-cellulose, Glutathione Sepharose 4B and $Ni^{2+}$-NTA agarose chromatography, respectively, the DNA fragments encoding for GST-Sap1 and Sap1 were inserted into the expression vector pET-28a at NheI and EcoRI sites for the GST-Sap1 DNA fragment and at NdeI and BamHI sites for the Sap1 DNA fragment. Both of the fusion proteins 6His-GST-Sap 1 and 6His-Sap 1 were well overexpressed in *E. coli* BL21(DE3)pLys cells and their amounts reached to ~25% of total cellular proteins. Both of 6His-GST-Sap1 and 6His-Sap1 are soluble in cell extracts containing 0.4M KCl. The cell extract containing 6His-GST-Sap1 or 6His-Sap1 was adjusted to salt concentration of 0.2 M with buffer A and then applied to Glutathione Sepharose 4B or $Ni^{2+}$-NTA agarose column, respectively. The columns were washed with buffer A containing 0.2M KCl to remove unbound proteins and other impurities. In the case of 6His-Sap1, the column was further washed with buffer A containing 0.2M KCl and 20 mM imidazole. The bound 6His-GST-Sap1 was first eluted with 10 mM glutathione and the remaining 6His-GST-Sap1 was eluted with 0.5% SDS. As indicated in FIG. 5, the purity of 6His-GST-Sap1 reached to ~20% and ~70% when it was eluted by 10 mM glutathione and 0.5% SDS, respectively. The result shown in FIG. 6 indicated that the 6His-Sap1 was eluted at 250 mM imidazole and its purity reached to ~70%. As indicated in FIG. 3A, the purity of the fusion protein 6His-SSB-Sap1 reached to ~96% after ssDNA-cellulose affinity chromatography. As shown in FIG. 2, the expression levels of 6His-SSB-Sap1, 6His-GST-Sap1 and 6His-Sap1 in *E. coli* cells were comparable and not much different, but after ssDNA-cellulose, Glutathione Sepharose 4B and $Ni^{2+}$-NTA agarose affinity chromatography, respectively, these three fusion proteins had apparently different levels of homogeneity, with 6His-SSB-Sap1 reaching to the highest purity.

Example 4

Figure 7:
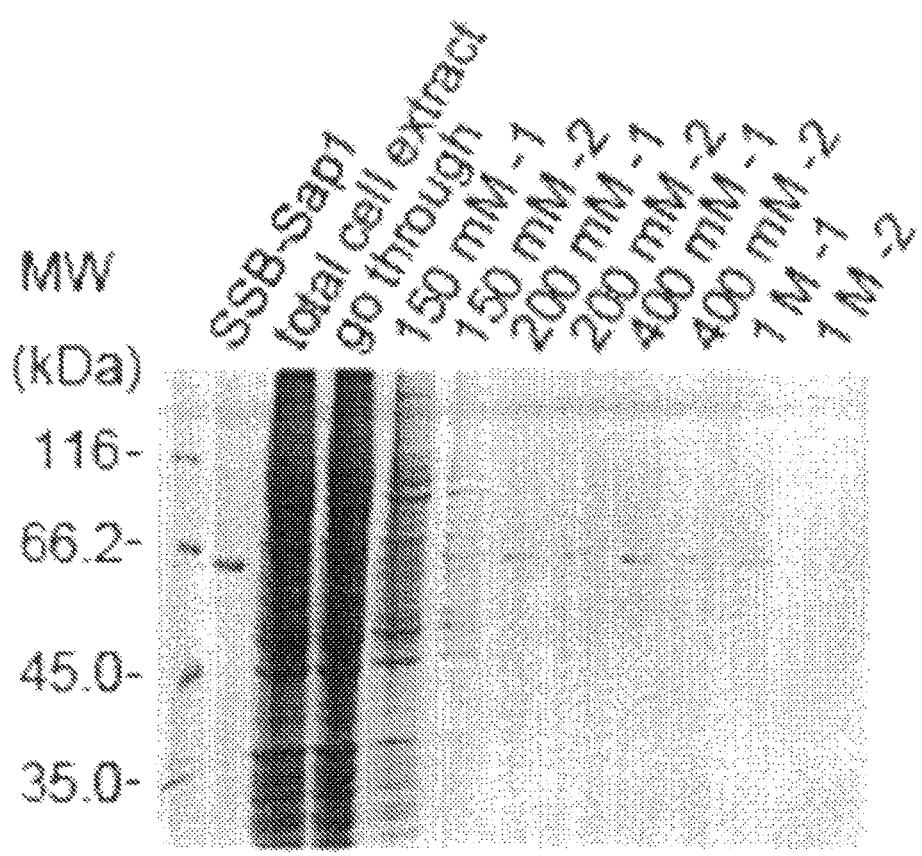
FIG. 7 shows the purification of SSB-Sap1 from human cell lysate. SSB-Sap1 was overexpressed in human cells. The human cell extract containing SSB-Sap1 was applied to ssDNA-cellulose column. By step elution, the majority of the bound SSB-Sap1 was eluted at salt concentration of 0.2 to 1.0 M KCl. The SSB-Sap1 lane in FIG. 7-9 indicates the position of this protein in SDS-PAGE gel.
Figure 8:
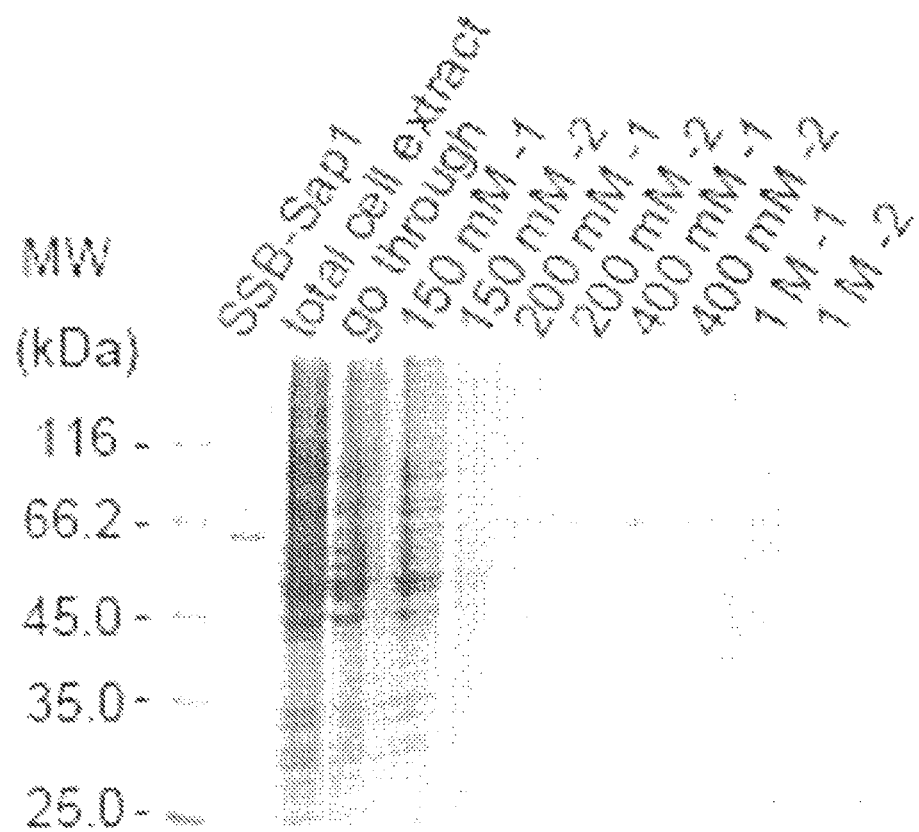
FIG. 8 shows the purification of SSB-Sap1 from insect cell lysate. SSB-Sap1 was overexpressed in insect cells. The insect cell extract containing SSB-Sap1 was applied to ssDNA-cellulose column. The majority of the bound SSB-Sap1 was eluted at salt concentration of 0.2 to 1.0 M KCl.
Figure 9:
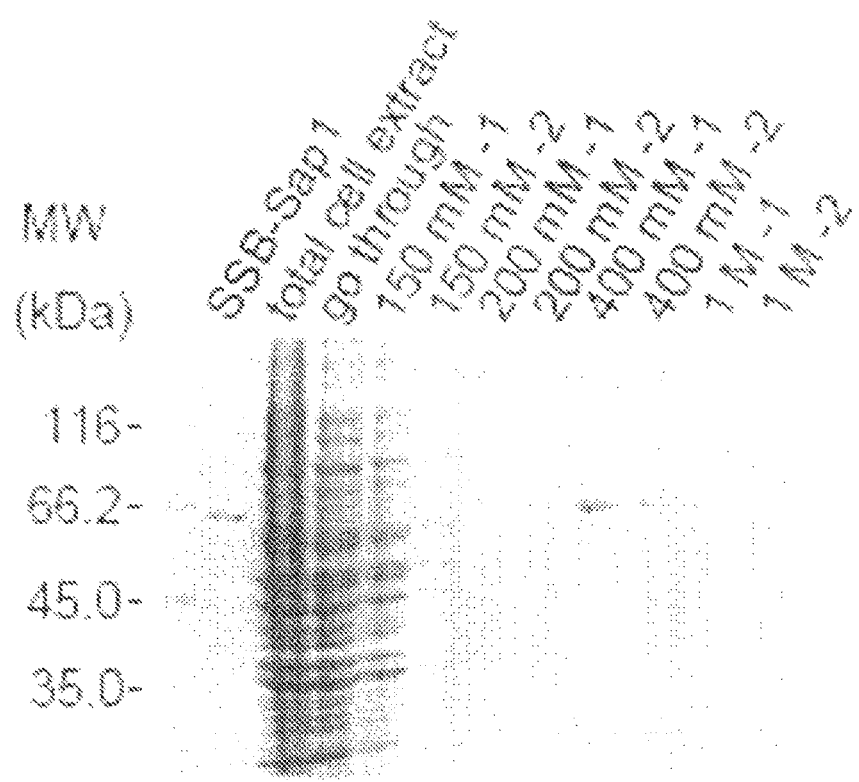
FIG. 9 shows the purification of SSB-Sap1 from yeast cell extract. SSB-Sap1 was overexpressed in the fission yeast S. pombe cells. The yeast cell extract containing SSB-Sap1 was applied to ssDNA-cellulose column. The majority of the bound SSB-Sap1 was eluted at salt concentration of 0.2 to 1.0 M KCl.

Overexpression of SSB-Sap1 in human, insect and the fission yeast *S. pombe* cells and purification of the SSB-Sap1 overexpressed in these cells with ssDNA-cellulose affinity chromatography With routine procedure, the recombinant plasmids were constructed to overexpress the fusion protein SSB-Sap1 in human, insect and the fission yeast *S. pombe* cells, respectively. The cell extract containing SSB-Sap1 was obtained and applied to ssDNA-cellulose column. The results in FIGS. 7, 8 and 9 indicated that the expression level of SSB-Sap1 was ~1% or less of the total cellular proteins in the above three expression systems. No matter whether SSB-Sap1 was overexpressed in human, insect, or yeast cells, SSB-Sap1 was soluble, bound to ssDNA-cellulose well and was eluted at salt concentrations of 0.2 to 1.0 M KCl. The purity of SSB-Sap1 reached to ~70%, ~80% and ~90% after ssDNA-cellulose chromatography when the SSB-Sap1 was overexpressed in human, insect and yeast cells, respectively.

Example 5

Removal of SSB from SSB-Fusion Protein

Figure 10:
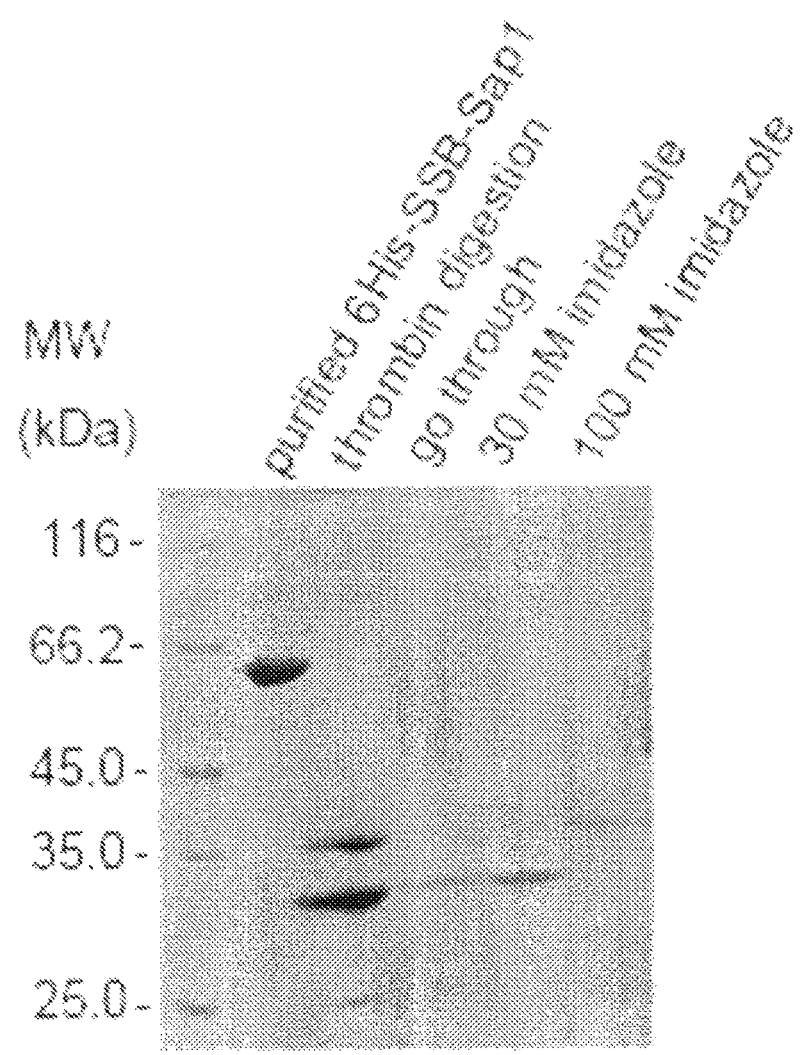
FIG. 10 shows the cleavage of 6His-SSB-Sap1 by thrombin and the removal of 6His-SSB by $Ni^{2+}$-NTA agarose column.

100 μg of 6His-SSB-Sap1 was incubated with one unit of thrombin in buffer A containing 0.1 M KCl and 2.5 mM $CaCl_2$ at room temperature for 2 to 5 hrs. As shown in FIG. 10, the fusion protein 6His-SSB-Sap1 was completely digested by thrombin and the 6His-SSB was removed through $Ni^{2+}$-NTA agarose column.

Similarly, more than a dozen of SSB-fusion proteins have been overproduced in *E. coli*, yeast, insect, or human cells. No matter whether the interest proteins or polypeptides are from prokaryotic or eukaryotic cells, all of these fusion proteins achieved good solubility. The overproduced SSB-fusion proteins are applied to ssDNA cellulose and all of them retain in the ssDNA-cellulose column well, indicating that the SSB fused to interest proteins or polypeptides maintains its capability of binding to ssDNA and the interest proteins or polypeptides do not spatially hinder the binding of SSB to ssDNA, which guarantees the good separation of SSB-fusion proteins from impurities through ssDNA-cellulose affinity chromatography.

All SSB-fusion proteins were designed to contain a cleavage site at the junction of SSB and interest proteins. The cleavage site permits the generation of interest proteins or polypeptides without the fused SSB. All purified SSB-fusion proteins are good substrates for cleavage by site-specific proteases such as thrombin or enterokinase. Preferably, the protease used is one that does not cleave the SSB and the interest protein. After cleavage, the SSB can be removed by absorption to ssDNA-cellulose or $Ni^{2+}$-agarose column if six histidines are fused to the N-terminus or C-terminus of the SSB.

The combination of high-level expression, high solubility, efficient purification, and site-specific proteolysis of fusion proteins will promise pSSB vectors a powerful system for expression and purification of interest proteins and polypeptides.

While the present invention has been described with reference to particular embodiments, it will be understood that the embodiments are illustrative and that the invention scope is not so limited. Alternative embodiments of the present invention will become apparent to those having ordinary skill in the art to which the present invention pertains. Such alternate embodiments are considered to be encompassed within the scope of the present invention. Accordingly, the scope of the present invention is defined by the appended claims and is supported by the foregoing description.

What is claimed is:

1. An expression vector comprising a promoter and a polynucleotide sequence encoding a fusion protein; wherein the fusion protein-encoding polynucleotide sequence is so operably linked to the promoter that the transcription of the fusion protein-encoding polynucleotide sequence is controlled by the promoter; wherein the fusion protein comprises a single-stranded DNA-binding protein and an interest protein or polypeptide fused directly or indirectly with the COOH-terminus or NH$_2$-terminus of the single-stranded DNA-binding protein;

wherein the single-stranded DNA-binding protein is capable of binding to single-stranded DNA; and
wherein the interest protein or polypeptide does not contain a physical feature that can be used for affinity purification;
so that the interest protein or polypeptide can be purified as a part of the fusion protein when the fusion protein is purified by binding to single-stranded DNA via the single-stranded DNA-binding protein.

2. The expression vector of claim 1, wherein said single-stranded DNA-binding protein is the single-stranded DNA-binding protein of bacteriophage T7 of SEQ ID NO 2, or a variant retaining the single-stranded DNA-binding capacity.

3. The expression vector of claim 1, wherein the fusion protein further comprises one or more purification tags selected from the group consisting of poly-histidine residues and glutathione-S-transferase.

4. The expression vector of claim 1, wherein the interest protein or polypeptide is fused to the single-stranded DNA binding protein through a cleavable linker.

5. The expression vector of claim 4, wherein the cleavable linker is cleavable by a site specific protease.

6. The expression vector of claim 5, wherein the cleavable linker is cleavable by enterokinase, thrombin, blood coagulation factor X$_a$, or rennin.

7. The expression vector of claim 1, wherein the single-stranded DNA binding protein is derived from species selected from the group consisting of bacteriophages, bacteria, archaebacteria, thermophilic bacteria, viruses, yeast, and eukaryotic cells from multiple-cell organisms.

8. The expression vector of claim 1, wherein the single-stranded DNA binding protein is derived from an artificial polynucleotide sequence encoding a polypeptide with the capacity of binding to single-stranded DNA.

9. The expression vector of claim 1, wherein the expression vector is derived from a plasmid selected from the group consisting of pSSB-B1 with a multi-cloning site of SEQ ID NO 3, pSSB-B2 with a multi-cloning site of SEQ ID NO 4, pSSB-B3 with a multi-cloning site of SEQ ID NO 5, pSSB-B4 with a multi-cloning site of SEQ ID NO 6, pSSB-Y1 with a multi-cloning site of SEQ ID NO 7, pSSB-Y2 with a multi-cloning site of SEQ ID NO 8, pSSB-I1 with a multi-cloning site of SEQ ID NO 9, pSSB-I2 with a multi-cloning site of SEQ ID NO 10, pSSB-I3 with a multi-cloning site of SEQ ID NO 11, pSSB-I4 with a multi-cloning site of SEQ ID NO 12, pSSB-H1 with a multi-cloning site of SEQ ID NO 13, pSSB-H2 with a multi-cloning site of SEQ ID NO 14, pSSB-H3 with a multi-cloning site of SEQ ID NO 15, and pSSB-H4 with a multi-cloning site of SEQ ID NO 16.

* * * * *

SEQUENCE LISTING

```
<160> NUMBER OF SEQ ID NOS: 18

<210> SEQ ID NO 1
<211> LENGTH: 699
<212> TYPE: DNA
<213> ORGANISM: Bacteriophage T7

<400> SEQUENCE: 1
atggctaaga agattttcac ctctgcgctg ggtaccgctg aaccttacgc ttacatcgcc      60
aagccggact acggcaacga agagcgtggc tttgggaacc ctcgtggtgt ctataaagtt     120
gacctgacta ttcccaacaa agacccgcgc tgccagcgta tggtcgatga aatcgtgaag     180
tgtcacgaag aggcttatgc tgctgccgtt gaggaatacg aagctaatcc acctgctgta     240
gctcgtggta agaaaccgct gaaaccgtat gagggtgaca tgccgttctt cgataacggt     300
gacggtacga ctacctttaa gttcaaatgc tacgcgtctt ccaagacaa gaagaccaaa      360 gagaccaagc acatcaatct ggttgtggtt gactcaaaag gtaagaagat ggaagacgtt     420
ccgattatcg gtggtggctc taagctgaaa gttaaatatt ctctggttcc atacaagtgg     480
aacactgcta taggtgcgag cgttaagctg caactggaat ccgtgatgct ggtcgaactg     540
gctacctttg gtggcggtga agacgattgg gctgacgaag ttgaagagaa cggctatgtt     600
gcctctggtt ctgccaaagc gagcaaacca cgcgacgaag aaagctggga cgaagacgac     660
gaagagtccg aggaagcaga cgaagacgga gacttctaa                             699

<210> SEQ ID NO 2
<211> LENGTH: 232
<212> TYPE: PRT
<213> ORGANISM: Bacteriophage T7

<400> SEQUENCE: 2

Met Ala Lys Lys Ile Phe Thr Ser Ala Leu Gly Thr Ala Glu Pro Tyr
  1               5                  10                  15
```

```
Ala Tyr Ile Ala Lys Pro Asp Tyr Gly Asn Glu Glu Arg Gly Phe Gly
            20                  25                  30

Asn Pro Arg Gly Val Tyr Lys Val Asp Leu Thr Ile Pro Asn Lys Asp
        35                  40                  45

Pro Arg Cys Gln Arg Met Val Asp Glu Ile Val Lys Cys His Glu Glu
    50                  55                  60

Ala Tyr Ala Ala Ala Val Glu Glu Tyr Glu Ala Asn Pro Pro Ala Val
65                  70                  75                  80

Ala Arg Gly Lys Lys Pro Leu Lys Pro Tyr Glu Gly Asp Met Pro Phe
                85                  90                  95

Phe Asp Asn Gly Asp Gly Thr Thr Thr Phe Lys Phe Lys Cys Tyr Ala
            100                 105                 110

Ser Phe Gln Asp Lys Lys Thr Lys Glu Thr Lys His Ile Asn Leu Val
        115                 120                 125

Val Val Asp Ser Lys Gly Lys Lys Met Glu Asp Val Pro Ile Ile Gly
    130                 135                 140

Gly Gly Ser Lys Leu Lys Val Lys Tyr Ser Leu Val Pro Tyr Lys Trp
145                 150                 155                 160

Asn Thr Ala Val Gly Ala Ser Val Lys Leu Gln Leu Glu Ser Val Met
                165                 170                 175

Leu Val Glu Leu Ala Thr Phe Gly Gly Gly Asp Asp Trp Ala Asp
            180                 185                 190

Glu Val Glu Glu Asn Gly Tyr Val Ala Ser Gly Ser Ala Lys Ala Ser
        195                 200                 205

Lys Pro Arg Asp Glu Glu Ser Trp Asp Glu Asp Glu Glu Ser Glu
    210                 215                 220

Glu Ala Asp Glu Asp Gly Asp Phe
225                 230

<210> SEQ ID NO 3
<211> LENGTH: 55
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (19)..(20)

<400> SEQUENCE: 3
gcccatgggc agcagcatgt tccatatggc tagcgacgac gacgacaagg gatcc          55

<210> SEQ ID NO 4
<211> LENGTH: 58
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (19)..(20)

<400> SEQUENCE: 4
gcccatgggc agcagcatgt tccatatggc tagcctggtg ccgcgcggca gcggatcc       58

<210> SEQ ID NO 5
<211> LENGTH: 73
<212> TYPE: DNA
<213> ORGANISM: Artificial
```

```
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (37)..(38)

<400> SEQUENCE: 5
gcccatgggc agcagccatc atcatcatca tcacatgttc catatggcta gcgacgacga      60
cgacaaggga tcc                                                         73

<210> SEQ ID NO 6
<211> LENGTH: 76
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (37)..(38)

<400> SEQUENCE: 6
gcccatgggc agcagccatc atcatcatca tcacatgttc catatggcta gcctggtgcc      60
gcgcggcagg ggatcc                                                      76

<210> SEQ ID NO 7
<211> LENGTH: 77
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)

<400> SEQUENCE: 7
ctcgagatgc atcatcatca tcatcacatg ttcgacgacg acgacaagcg cggccgcagg      60
tcgacagatc tcccggg                                                     77

<210> SEQ ID NO 8
<211> LENGTH: 80
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)

<400> SEQUENCE: 8
ctcagaatgc atcatcatca tcatcacatg ttcatggtgc cgcgcggcag ccgcggcgcg      60
aggtcgacag atctcccggg                                                  80

<210> SEQ ID NO 9
<211> LENGTH: 51
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (12)..(13)

<400> SEQUENCE: 9
```

```
ctcgagatgg ctttcgacga cgacgacaag ggatccagtg aattcctgca g          51
```

<210> SEQ ID NO 10
<211> LENGTH: 54
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (12)..(13)

<400> SEQUENCE: 10

```
ctcgagatgg ctttcctggt gccgcgcggc agcggatcca gtgaattcct gcag       54
```

<210> SEQ ID NO 11
<211> LENGTH: 69
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)

<400> SEQUENCE: 11

```
ctcgagatgc atcaccacca tcaccatgct ttcgacgacg acgacggagg atccagtgaa   60
ttcctgcag                                                           69
```

<210> SEQ ID NO 12
<211> LENGTH: 72
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)
<223> OTHER INFORMATION: location for insertion of the fusion protein of
      SSB and another protein
<220> FEATURE:
<221> NAME/KEY: location for insertion of the fusion protein of SSB and
      another protein
<222> LOCATION: (30)..(31)

<400> SEQUENCE: 12

```
ctcgagatgc atcaccacca tcaccatgct ttcctggtgc cgcgcggcag cggatccagt   60
gaattcctgc ag                                                       72
```

<210> SEQ ID NO 13
<211> LENGTH: 51
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (12)..(13)

<400> SEQUENCE: 13

```
ctcgagatgg ctttcgacga cgacgacaag ggatccagtg aattcctgca g           51
```

<210> SEQ ID NO 14
<211> LENGTH: 54

```
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (12)..(13)

<400> SEQUENCE: 14
ctcgagatgg ctttcctggt gccgcgcggc agcggatcca gtgaattcct gcag         54

<210> SEQ ID NO 15
<211> LENGTH: 69
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)

<400> SEQUENCE: 15
ctcgagatgc atcaccacca tcaccatgct ttcgacgacg acgacaaggg atccagtgaa   60
ttcctgcag                                                           69

<210> SEQ ID NO 16
<211> LENGTH: 72
<212> TYPE: DNA
<213> ORGANISM: Artificial
<220> FEATURE:
<223> OTHER INFORMATION: multiple enzymatic linker
<220> FEATURE:
<221> NAME/KEY: location for insertion of the fusion protein of SSB and
      another protein
<222> LOCATION: (30)..(31)

<400> SEQUENCE: 16
ctcgagatgc atcaccacca tcaccatgct ttcctggtgc cgcgcggcag cggatccagt   60
gaattcctgc ag                                                       72

<210> SEQ ID NO 17
<211> LENGTH: 765
<212> TYPE: DNA
<213> ORGANISM: Schizosaccharomyces pombe
<220> FEATURE:
<221> NAME/KEY: sap1
<222> LOCATION: (1)..(765)

<400> SEQUENCE: 17
atggaagctc ccaagatgga actgaagagc tataaacgaa agaatgcttc gttatctccc   60
agttcctctc ccgccaaggc acagcgtact cacttgtcct tggaggaaaa aatcaagctc  120
atgcgcttag tcgtgcgtca caagcacgaa ctcgtcgacc gtaaaactag tgagttttac  180
gccaagatcg cccgtatcgg ttatgaggac gagggcctcg ctattcatac cgagtccgcc  240
tgtcgcaatc aaatcatctc catcatgcgc gtctacgaac agcgtttggc ccatcgtcaa  300
cccggcatga agaccactcc cgaagaggat gagctcgacc aactttgcga tgaatggaag  360
gcccgtctca gcgagctcca acagtatcgc gaaaaattct tggttggcaa gcgcaagtgt  420
gattgcaatg atgaaattaa tgaacgtctc aagaagctca ctgaagagca acaaaacgtc  480
gacatgcttg tcgccaaggt caactttctc tccaaacatc ttcacgataa tgaggaaaaa  540
ttaatgcagg taaatgctaa aatggatgaa gttcttgccg aaaataagcg ccttcaacaa  600
```

-continued

```
cttctcgatc ataacgattt gttgtccaag ctcgagcctc cctctgctta cgctccccat    660
ggcgttaaca tgggcactaa tatgggtgcc aacatgggcg ctaatatgaa tgccattcgt    720
ggcggtctcc attctagcat ctctcctaat cttggtgacc attaa                    765
```

<210> SEQ ID NO 18
<211> LENGTH: 1143
<212> TYPE: DNA
<213> ORGANISM: Schizosaccharomyces pombe
<220> FEATURE:
<221> NAME/KEY: fen1
<222> LOCATION: (1)..(1143)

<400> SEQUENCE: 18

```
atgggaatta aaggtttggc tcaagtacta agcgagcatg ccccagccag tgtcaaacat     60
aatgatatta aaaattattt tggacggaaa gtggctatag atgcgtcaat gagtctttat    120
caatttttaa ttcaagttcg cagtcaagat ggtcaacagc taatgaatga acaaggcgag    180
actactagtc atttaatggg aatgttttat cgtacactcc gaattgtcga taatggaata    240
aagccttgct ttgtctttga tggaaaacca ccaacattga agtcagggga attagctaaa    300
cgtgtggccc gacatcaaaa agcacgagag atcaagagg agacaaaaga ggttggtaca    360
gctgaaatgg tggatcggtt tgccaaacgt acggtcaaag ttactcggca acataatgac    420
gaagcaaaac gtttactaga gttaatggga attcccttcg ttaacgcacc ctgtgaagca    480
gaagctcaat gtgccgcttt agcccgttca ggaaaagttt atgctgctgc ttctgaggac    540
atggacacat tgtgcttcca agctcctgta cttttgagac acctgacatt tagtgagcaa    600
agaaaggaac caattagtga gtataacata gaaaaagcat tgaatggttt agatatgtcg    660
gtggagcagt ttgtagactt tgtgtattct ttggggttgtg actattgtga acctattcgg    720
ggagttggcc ccgctagagc cgtcgagtta attaggcaat acgggactct cgatcgcttt    780
gtcaaagagg cggatcgatc aaaatatcct attccggaag attggcctta tgaagatgcc    840
agaagactgt ttttggatgc agaagtactt cctggtgaag agattgagtt gaaatggaaa    900
agtcccgatg cagatggcat tatacaattt ctggttaagg aaaaaggttt caatgaagat    960
cgtgttaaat tggggatcaa tagactagaa aaagcctcaa agacaattcc acagggtcgt   1020
cttgattcct tttttaaacc agtcccttct tctcccaaaa aacctgtaga tacaaagagc   1080
aaaggatcag caaaaaggaa aagagattca aataagggtg gtgaaagcaa gaaaaagcgt   1140
tga                                                                1143
```